United States Patent [19]

Martin

[11] Patent Number: 5,733,284
[45] Date of Patent: Mar. 31, 1998

[54] DEVICE FOR ANCHORING SPINAL INSTRUMENTATION ON A VERTEBRA

[75] Inventor: Jean-Raymond Martin, Tournefeuille, France

[73] Assignee: Paulette Fairant, Tournefeuille, France

[21] Appl. No.: 605,037

[22] PCT Filed: Jul. 15, 1994

[86] PCT No.: PCT/FR94/00888

§ 371 Date: Feb. 27, 1996

§ 102(e) Date: Feb. 27, 1996

[87] PCT Pub. No.: WO95/05785

PCT Pub. Date: Mar. 2, 1995

[30] Foreign Application Priority Data

Aug. 27, 1993 [FR] France ................................ 93 10291
Feb. 7, 1994 [FR] France ................................ 94 01439

[51] Int. Cl.⁶ ...................................................... A61B 17/56
[52] U.S. Cl. ........................................... 606/61; 606/74
[58] Field of Search ................................ 606/61, 53, 72, 606/74, 60, 86, 105, 69, 70, 71, 151, 76, 77

[56] References Cited

U.S. PATENT DOCUMENTS

| | | |
|---|---|---|
| 3,865,105 | 2/1975 | Lode . |
| 3,905,777 | 9/1975 | LaCroix .................... 606/76 |
| 3,906,550 | 9/1975 | Rostoker et al. ............ 606/76 |
| 3,977,397 | 8/1976 | Kalnberz et al. . |
| 4,078,599 | 3/1978 | Nissinen . |
| 4,271,836 | 6/1981 | Bacal et al. . |
| 4,289,123 | 9/1981 | Dunn . |
| 4,386,603 | 6/1983 | Mayfield . |
| 4,445,513 | 5/1984 | Ulrich et al. . |
| 4,448,191 | 5/1984 | Rodnyansky et al. . |
| 4,554,914 | 11/1985 | Kapp et al. ................ 606/69 |
| 4,611,582 | 9/1986 | Duff . |
| 4,697,582 | 10/1987 | William .................... 606/61 |
| 4,836,196 | 6/1989 | Park et al. . |
| 4,854,496 | 8/1989 | Bugle . |
| 4,946,458 | 8/1990 | Harms et al. . |
| 5,011,484 | 4/1991 | Bréard ...................... 606/61 |
| 5,108,399 | 4/1992 | Eitenmuller et al. ........ 606/77 |
| 5,219,349 | 6/1993 | Krag et al. . |
| 5,281,223 | 1/1994 | Ray . |
| 5,415,659 | 5/1995 | Lee et al. ................... 606/61 |
| 5,439,463 | 8/1995 | Lin .......................... 606/61 |
| 5,531,747 | 7/1996 | Ray .......................... 606/70 |

FOREIGN PATENT DOCUMENTS

| | | |
|---|---|---|
| 0140790 | 5/1985 | European Pat. Off. . |
| 0260044 | 3/1988 | European Pat. Off. . |
| 0418387 | 3/1991 | European Pat. Off. . |
| 0499037 | 8/1992 | European Pat. Off. . |
| 0470660 | 12/1992 | European Pat. Off. . |
| 1397395 | 3/1965 | France . |
| 2689750 | 10/1992 | France . |
| 2697744 | 5/1994 | France . |
| 2845647 | 8/1980 | Germany . |
| 3807346 | 6/1989 | Germany . |
| 848009 | 8/1979 | U.S.S.R. . |
| 780652 | 8/1957 | United Kingdom . |
| 2162065 | 1/1986 | United Kingdom . |
| 2198647 | 6/1988 | United Kingdom . |
| 8504096 | 9/1985 | WIPO . |
| 9002527 | 3/1990 | WIPO . |
| 9213496 | 8/1992 | WIPO . |

Primary Examiner—Michael Buiz
Assistant Examiner—Julian W. Woo
Attorney, Agent, or Firm—Harold H. Dutton, Jr.

[57] ABSTRACT

A device for anchoring rachidian instrumentation on a vertebra, comprising at least one support, a carrier for coupling the instrumentation to the support and a structure for anchoring the support with respect to the vertebra, the support having a convex face shaped to conform to and lie against at least one portion of the concave surface of the posterior arch of the vertebra on one side of the spinous process of the vertebral column, and the anchoring structure rigidly linking at least two distinct parts of the support to at least two correspondingly distinct portions of the vertebra.

14 Claims, 10 Drawing Sheets

DEVICE FOR ANCHORING SPINAL INSTRUMENTATION ON A VERTEBRA

This invention relates to a device for anchoring spinal instrumentation on a vertebra.

BACKGROUND AND OBJECTS OF THE INVENTION

The known implanted spinal osteosynthesis devices are fixed with respect to the various vertebrae by anchoring elements.

Anchoring elements are already known which are constituted by, or which have, intrapedicular screws. These intrapedicular screws are widely used, in various forms, with different types of osteosynthesis devices (Cotrel-Dubousset, Roy-Camille, etc.).

Anchoring elements in the form of hooks with curved, fixed ends supported on the articular processes, or on the lamina or on a transverse process of the vertebra, are also known. The hook is held in position against the bone and kept there by spinal instrumentation.

Anchoring devices in the form of sub-laminar wires (de Luque-type osteosynthesis devices) are also known.

All these known anchoring elements have disadvantages as regards reliability and longevity and/or the strength of the anchorage thus brought about, especially as they bring about a single anchorage in each of the paravertebral grooves. In actual fact, all these anchoring elements are essentially constituted by a hard, rigid metal element supported on a single localized zone on one side of the vertebra. Now these anchoring elements are intended to transmit extremely high stresses caused by the instrumentation on the various vertebrae. For this reason, one of the greatest risks limiting the longevity and reliability of the spinal instrumentations originates from the fact that the anchoring elements may become detached or break the bone in the event of excessively high mechanical stresses. Hooks and screws, in particular, induce a high degree of discontinuity between the instrumentation and the vertebra, from the point of view of mechanical characteristics. Thus, the local contact surface zone between the anchoring device and the osseous portion of vertebra is subjected to heavy tensile stresses which are liable to give rise to secondary osteolysis.

Moreover, sub-laminar wires have the disadvantage of causing to major neurological risks and cannot be used with all categories of spinal instrumentation.

American patent U.S. Pat. No. 4,836,196 describes a spacer device composed of a plastics material which makes it possible to reduce the stresses transmitted between a screw fitted into the osseous part of the vertebra, and the instrumentation. A device of this kind can nevertheless not be used with most of the known spinal instrumentations and induces a flexibility in the coupling between the instrumentation and the anchoring device which may prove harmful.

French patent application FR-A-2 689 750 describes a spinal osteosynthesis device comprising hooks and/or intrapedicular screws and plates for coupling the instrumentation which are anchored in the vertebra by means of an intrapedicular screw. In that instance, too, the anchorage brought by a single intrapedicular screw proves insufficient.

The aim of the invention is therefore to alleviate the disadvantages of the known anchoring devices.

The general aim of the invention is therefore to propose an anchoring device for implanted spinal instrumentation, such as a spinal osteosynthesis device or a dynamic implanted vertebral orthosis, which offers greater reliability, longevity and strength than the known anchoring devices. The aim of the invention is also to propose a vertebral anchoring device which leaves vertebral, posterior articular and ligamentary systems unaffected, an essential precondition for the insertion of equipment intended to correct and preserve physiological movements of the vertebral column.

DESCRIPTION OF THE INVENTION

The aim of the invention is also to propose an anchoring device of this kind which can be used with, and adapted to, most of the spinal instrumentations.

In order to accomplish this, the invention relates to a device for anchoring spinal instrumentation onto a vertebra, comprising at least one support carrying means for coupling the instrumentation to the said support and means for anchoring the support with respect to the vertebra, wherein the support has a convex face which fits, and bears with contact against, at least one portion of the concave surface of the posterior arch of the vertebra on at least one side of the spinous process, and wherein the anchoring means rigidly link at least two distinct portions of the support with at least two corresponding distinct parts of the vertebra.

According to the invention, the said device has at least one support, the convex face of which extends facing the spinous process and/or at least one transverse process and/or at least one pedicle of the vertebra, and means for anchoring the said support, respectively, onto the spinous process and/or at least one transverse process and/or at least one pedicle of the vertebra.

According to the invention, each support is formed by a plate carrying coupling means and covering a portion of the concave surface of the posterior arch of the vertebra on at least one side of the spinous process.

A device according to the invention may have two supports, one on each side of the spinous process of the vertebra, or a single support extending on only one side, or on both sides, of the spinous process. When the device in the invention has two supports, it has means for coupling the instrumentation which are carried by only one, or by each, of the two supports. Advantageously and in accordance with the invention, the two supports are, together, linked with the same spinous process by common anchoring means. The spinous process, the cortical part of which is left completely unaffected, is thus buttressed and therefore supports and unites the two bilateral supports. The whole of the posterior vertebral arch serves as an anchorage, even for unilateral instrumentation.

According to the invention, the means for anchoring each support have at least one hook which is articulated on the support about a spindle, the said hook carrying a clamping screw fitted into a threaded hole in the hook, the said screw being supported either directly or indirectly on the support or on another hook, so as to cause the hook to pivot about its spindle in the direction in which the free end of the hook is clamped onto the corresponding part of the vertebra. Advantageously and in accordance with the invention, the anchoring means have at least one clamping claw formed by two hooks which are articulated on the same spindle or on parallel spindles and the mutually facing free ends of which are clamped towards one another.

According to the invention, the means for anchoring each support have at least one flange for clamping one end of the support onto a vertebral process, and particularly onto a spinous and/or transverse process.

Moreover, according to the invention, the convex face of a support is formed by a porous metal and is advantageously covered with a layer of hydroxy apatite.

The invention also relates to an anchoring device having, in combination, all or some of the characteristics mentioned above or below.

DESCRIPTION OF THE DRAWINGS

Other characteristics and advantages of the invention will emerge from the detailed description which follows with reference to the attached drawings, in which.

DETAILED DESCRIPTION OF THE PREFERRED EMBODIMENTS

Figure 1:
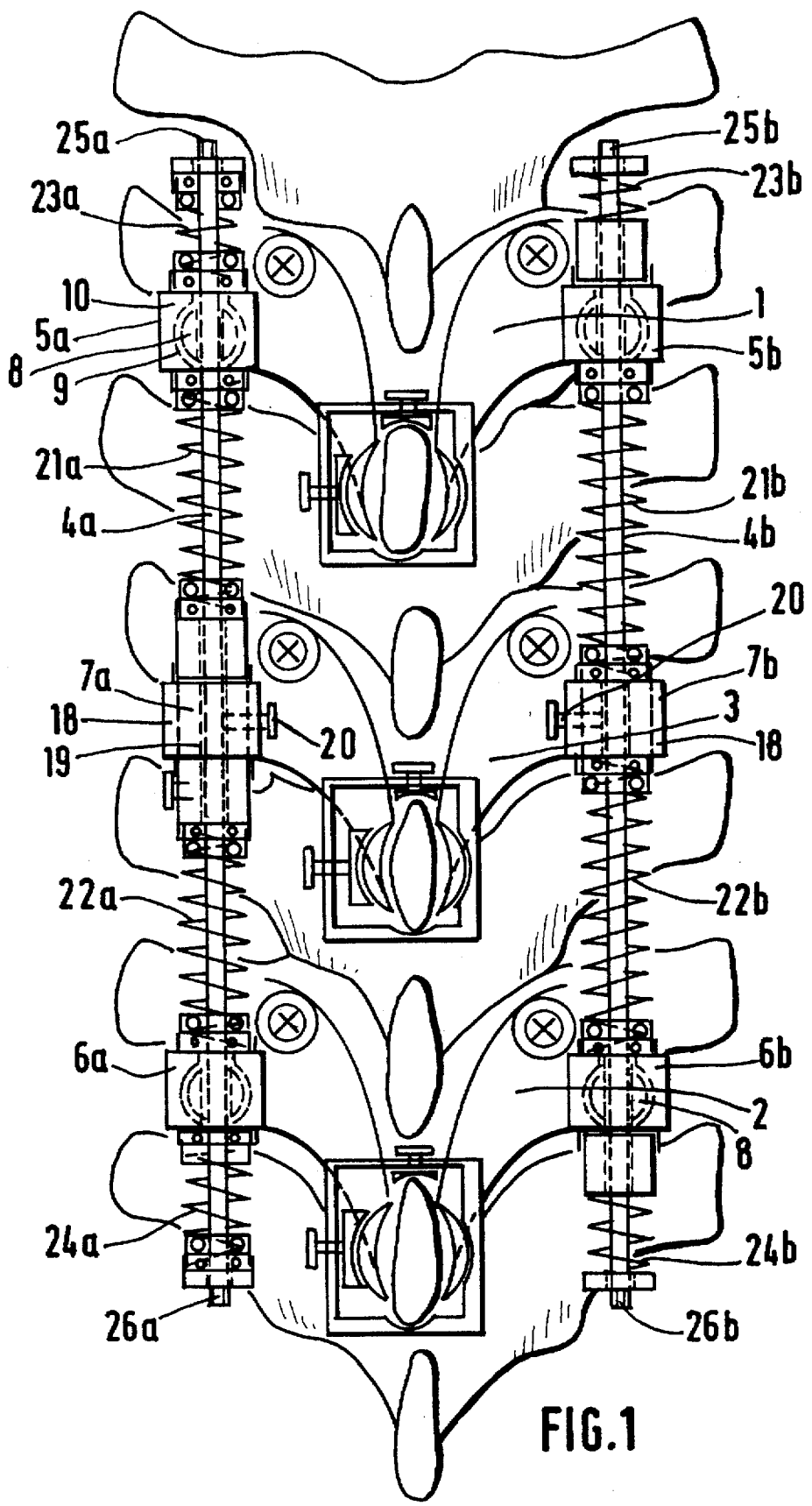
FIG. 1 is a diagrammatic rear view of an implanted dynamic vertebral orthosis, which is more particularly intended for the treatment of a scoliosis and is equipped with anchoring devices according to the invention.
Figure 10:
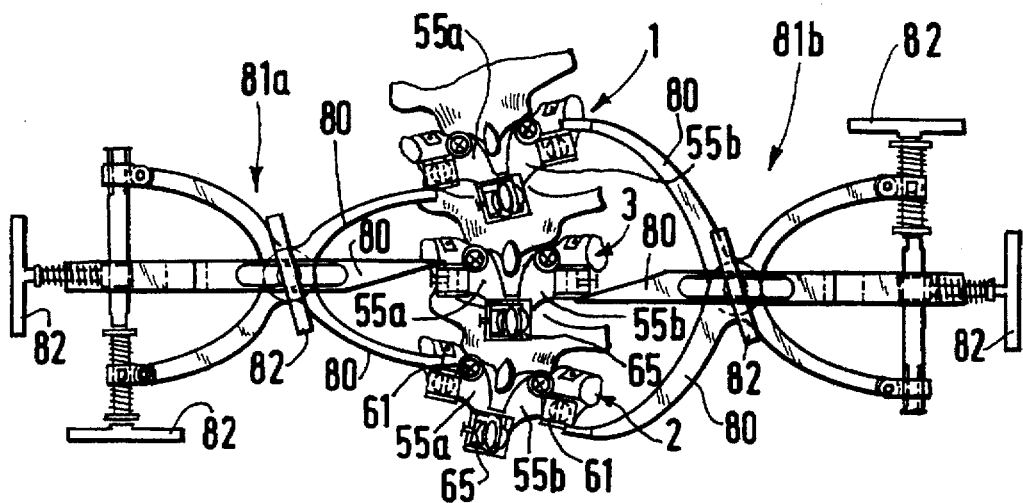
FIG. 10 is a diagrammatic rear view illustrating one stage in the placing in position of an orthosis equipped with anchoring devices according to the invention.

FIG. 1 represents an example of an implanted vertebral orthosis which makes it possible to carry out and maintain a correction of the relative position of five dorsal vertebrae, for treating a deformation of the scoliotic type. Before the placing of the orthosis in position, the vertebrae have a curvature with a convexity which is orientated towards the right (FIG. 10). The orthosis comprises an anchoring device 1 fixed to the upper end vertebra, an anchoring device 2 fixed to the lower end vertebra, and an anchoring device 3 fixed to the median vertebra located in the centre of the original curvature of the scoliosis. Thus, the orthosis instruments five successive vertebrae and is anchored onto three vertebrae.

The orthosis also has rods 4a, 4b extending laterally on each side of the spinous processes, namely a left-hand rod 4a located in the concavity of the deformation to be corrected, and a right-hand rod 4b located beside the convexity of the deformation to be corrected. Each rod 4a, 4b is a rod which is curved, flexible and elastic in flexion and made of biocompatible material such as a metal alloy (stainless steel or titanium) and/or of composite material. Each rod 4a, 4b is linked with the anchoring elements 1, 2, 3 on the vertebrae by coupling means 5a, 5b, 6a, 6b, 7a, 7b.

Figure 4:
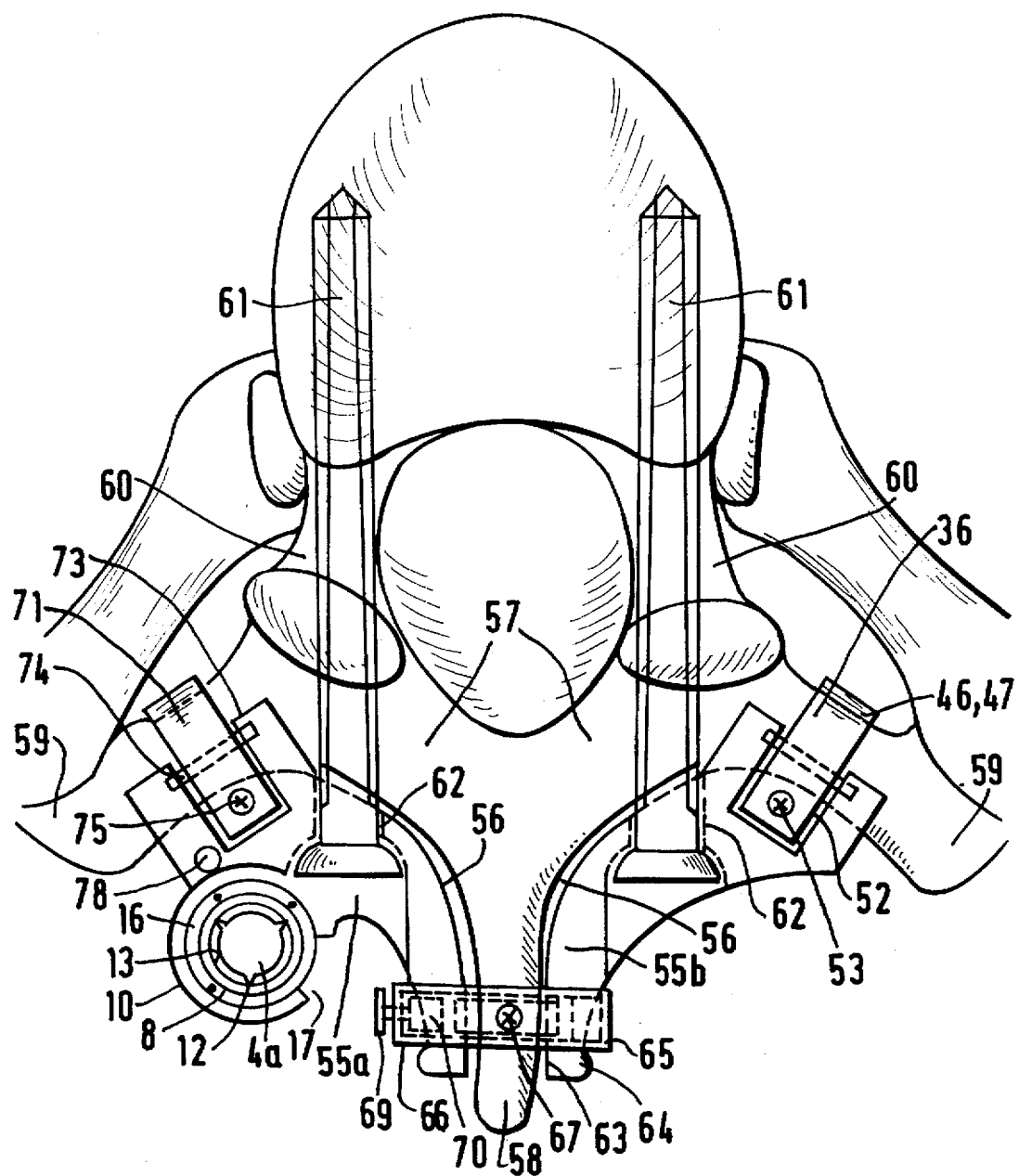
FIG. 4 is a diagrammatic view, in section through a horizontal plane, of FIG. 3.

The means 5a for coupling the left-hand rod 4a to the upper anchoring device 1 on the upper instrumented vertebra have a sphere 8 mounted in a freely rotating manner and enclosed in a spherical housing 9 in a cylinder 10 integral with the anchoring device 1, so as to form a connecting ball joint. The sphere 8 is perforated by a cylindrical bore 11 through which the rod 4a passes and in which the said rod 4a is able to slide in longitudinal axial translation in the vertical direction. The width of the bore 11 corresponds to the width of the rod 4a and the sphere 8 is fitted into the housing 9 without any possibility of relative movements in horizontal translation, particularly in the lateral and anteroposterior directions of the vertebra. In this way, the coupling means 5a thus brought about prohibit, after the placing in position of the rod 4a, any relative movement of the latter in horizontal translation with respect to the anchoring elements 1 and to the corresponding vertebra. On the other hand, the said coupling means 5a permit, after the placing of the rod in position, a relative movement in four other degree of freedom: a sliding movement in relative longitudinal translation along a vertical axis of the rod 4a and three degrees of freedom of rotation of the sphere 8 with respect to the cylinder 10, namely a relative rotation about an axis perpendicular to the frontal plane, a relative rotation about an axis perpendicular to a sagittal plane, and a relative rotation about a vertical axis. All the rotating movements are preferably performed by the sliding of the sphere 8 in rotation within the spherical housing 9. On the other hand, translation along the vertical axis takes place with the rod 4a in contact with the bore 11 in the sphere 8. The bore 11 is cylindrical in revolution. And, as shown in FIG. 4, the rod 4a is provided with ribs 12 regularly distributed around its axis and extending along the rod 4a in a projecting manner with respect to its outer face so as to make contact along the inner face of the bore 11. In the example represented, three ribs of triangular transverse cross-section are provided. In this way, contact frictions are reduced. The materials constituting the sphere 8 and cylinder 10 are chosen so as to permit rotating movements of the said sphere 8 within the housing 9, as indicated above. For example, the sphere 8 is made of metal alloy with a high surface quality, or of ceramics, and the cylinder 10 is constituted by a block of synthetic material such as polyethylene or other material. The sphere 8 and/or the cylinder 10 may be constituted by a self-lubricating material or else have a coating made of this material.

The cylinder 10 has an upper aperture 14 and a lower aperture 15 which permit the passage of the rod 4a and the dimensions of which, in terms of width, are greater than those of the rod 4a, in order to permit inclining movements of the latter with respect to the axis of the cylinder under the effect of the above-mentioned rotational movements. The dimensions of the apertures 14 and 15 are preferably such that they permit an amplitude of inclination of the rod 4a of at least 45° with respect to the vertical axis of the cylinder 10.

Figure 3:
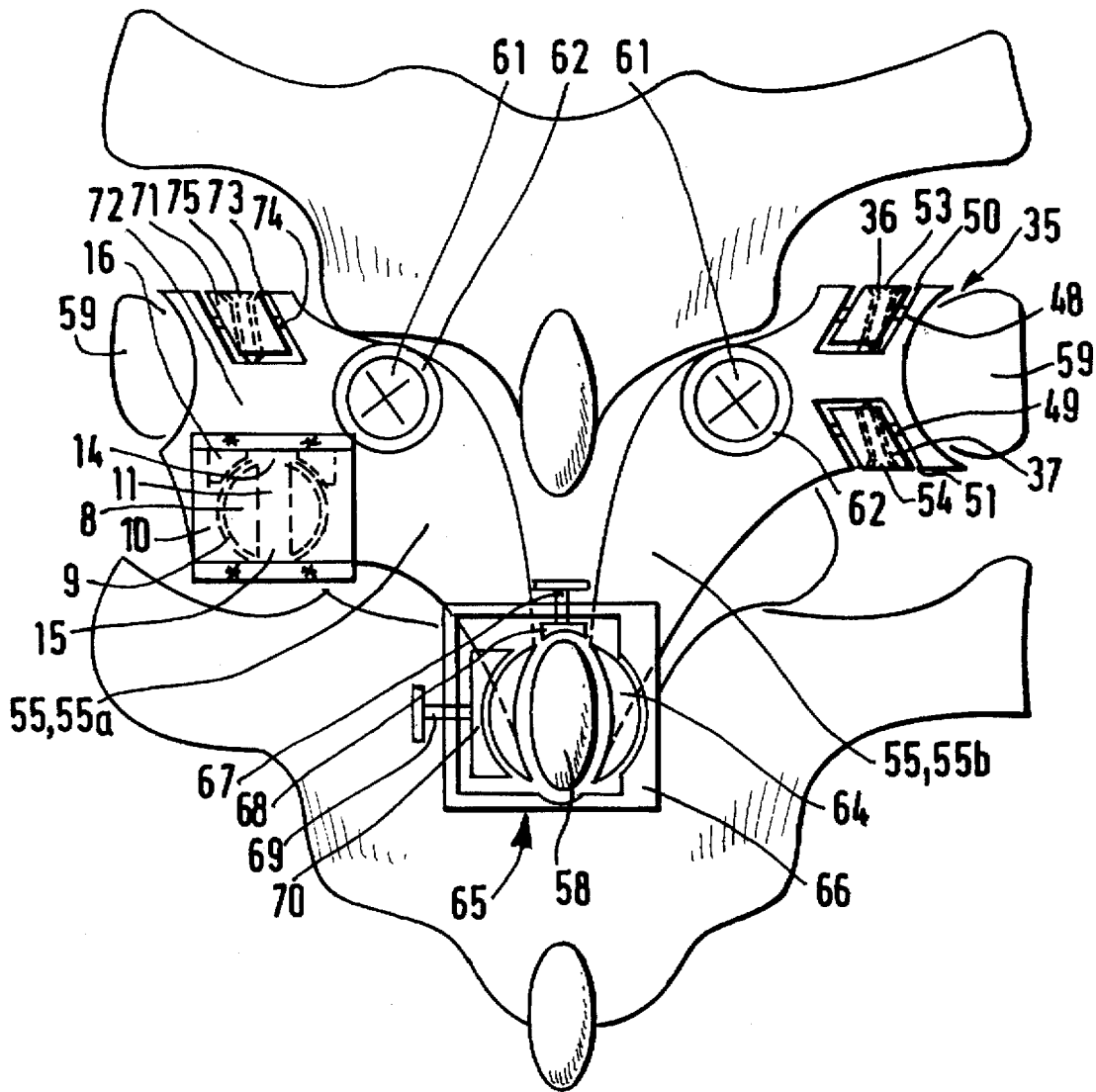
FIG. 3 is a diagrammatic rear view of a first mode of embodiment of an anchoring device according to the invention.

The sphere 8 is fitted into the spherical housing 9 when the rod 4a is placed in position. In order to accomplish this, a threaded crown 16 may be fitted at an upper end (or, in a variant which is not represented, at a lower end) of the cylinder 10 which has a housing for receiving the said crown 16, which housing is provided with a corresponding tapped hole (FIGS. 3 and 4). The crown 16 has an axial perforation which determines the upper aperture 14 of the cylinder 10 emerging into the spherical housing 9. The dimensions of the housing for receiving the crown 16 are defined so as to permit the insertion of the sphere 8 into the spherical housing 9 via the top or bottom. The lower face of the crown 16 has a concave shape in the form of a portion of a sphere so that it constitutes an extension of the spherical internal face of the housing 9 while enclosing the sphere 8 in the said housing 9 (FIG. 3). In a variant (FIG. 1), the cylinder is formed by a block of synthetic material and the upper (or lower) aperture 14 has a diameter slightly smaller than that of the sphere 8 which can be fitted forcibly into the housing 9 via the said aperture 14 which then retains the sphere 8 in the housing 9.

Before the introduction of the sphere 8 into the housing 9, the rod 4a is introduced into the inside of the cylinder 10. In order to accomplish this, the cylinder 10 is provided, over its entire height, with a slot 17 which communicates with the housing 9 and the width of which corresponds to the largest diameter envisaged for the rod 4a. The said slot 17 may be located on the inner side of the cylinder 10 facing the spinous processes, as represented in FIG. 4, or on the opposite side, or even on the rear side. However, the said slot 17 is preferably made in a portion of the cylinder 10 which undergoes the least tensile stresses in the horizontal radial direction. For installing the whole assembly, the sphere 8 is fitted around the rod 4a by introducing the latter through the bore 11, the rod 4a is introduced into the housing 9 through the slot 17 while keeping the sphere 8 above or below the cylinder 10, and the sphere 8 is then fitted into the housing 9. The crown 16, if present, is then screwed into the corresponding housing of the cylinder 10. The said crown 16 will have been previously fitted around the rod 4a above (or below) the sphere 8. The diameter of the rods 4a, 4b, which are adaptable to the same anchoring devices 1, 2, 3, may thus vary, the adaptation being brought about using spheres 8, the bore 11 in which corresponds to the diameter of the rods 4a, 4b.

The means 6a for coupling the rod 4a with respect to the lower anchoring device 2 of the lower end vertebra are identical to the means 5a previously described for coupling the said rod 4a to the upper anchoring device 1 of the upper end vertebra. On the other hand, the means 7a for coupling the rod 4a to the median anchoring device 3 of the median vertebra are rigid linking means prohibiting any relative movement of the rod 4a with respect to the anchoring device 3. In order to accomplish this, the said coupling means 7a are constituted by a cylinder 18 which is installed so as to be integral with the anchoring device 3 and provided with a cylindrical bore 19 over its entire height through which the rod 4a passes. The said bore 19 is similar to the bore 11 in the coupling means 5a previously described, and therefore has shapes and dimensions which correspond to those of the rod 4a. Furthermore, the cylinder 18 carries one or more screws 20 for the transverse locking of the rod 4a. The screw 20 is fitted into a corresponding threaded hole in the cylinder 18, which hole emerges into the bore 19. When the screw 20 is tightened, it bears on the rod 4a and locks it in translation with respect to the bore 19. In order to promote the said locking, the rod 4a may be provided with one or more horizontal peripheral grooves. The cylinder 18 is likewise provided with a slot over its entire height for the installation of the rod 4a.

The rod 4a located on the right of the spinous processes (FIG. 1) is linked with the anchoring devices 1, 2, 3 by coupling means 5b, 6b, 7b which are identical to the coupling means 5a, 6a, 7a previously described for the left-hand rod 4a.

The orthosis represented in FIG. 1 additionally has springs 21a, 21b, 22a, 22b, 23a, 23b, 24a, 24b acting on the anchoring devices for at least one vertebra. In the mode of embodiment in FIG. 1, the orthosis has, for each rod 4a, 4b, a spiral spring 21a, 21b interposed between the anchoring devices 1, 3 for the upper vertebra and median vertebra, a spiral spring 22a, 22b interposed between the anchoring devices 2, 3 for the lower vertebra and the median vertebra, a spiral spring 23a, 23b interposed between the anchoring device 1 for the upper vertebra and an upper free end 25a, 25b of the rod 4a, 4b, and a spiral spring 24a, 24b interposed between the anchoring device 2 for the lower vertebra and the lower free end 26a, 26b of the rod 4a, 4b. Each spiral spring 21a, 21b, 22a, 22b is interposed between the anchoring devices 1, 3 and 3, 2 for two distinct vertebra and has one end linked with the anchoring device 1 or 3 for 1 vertebra, and the other end linked with the anchoring device 3 or 2 for another vertebra. The springs 21a, 22a, 23a, 24a surround the rod 4a located on the concave side of the malformation to be corrected and are compression springs. The springs 21b, 22b, 23b, 24b surround the rod 4b located on the convex side of the deformation to be corrected and are traction springs. Each spring may also be used in torsion and associated with means for fixing its ends in torsion.

Figure 2:
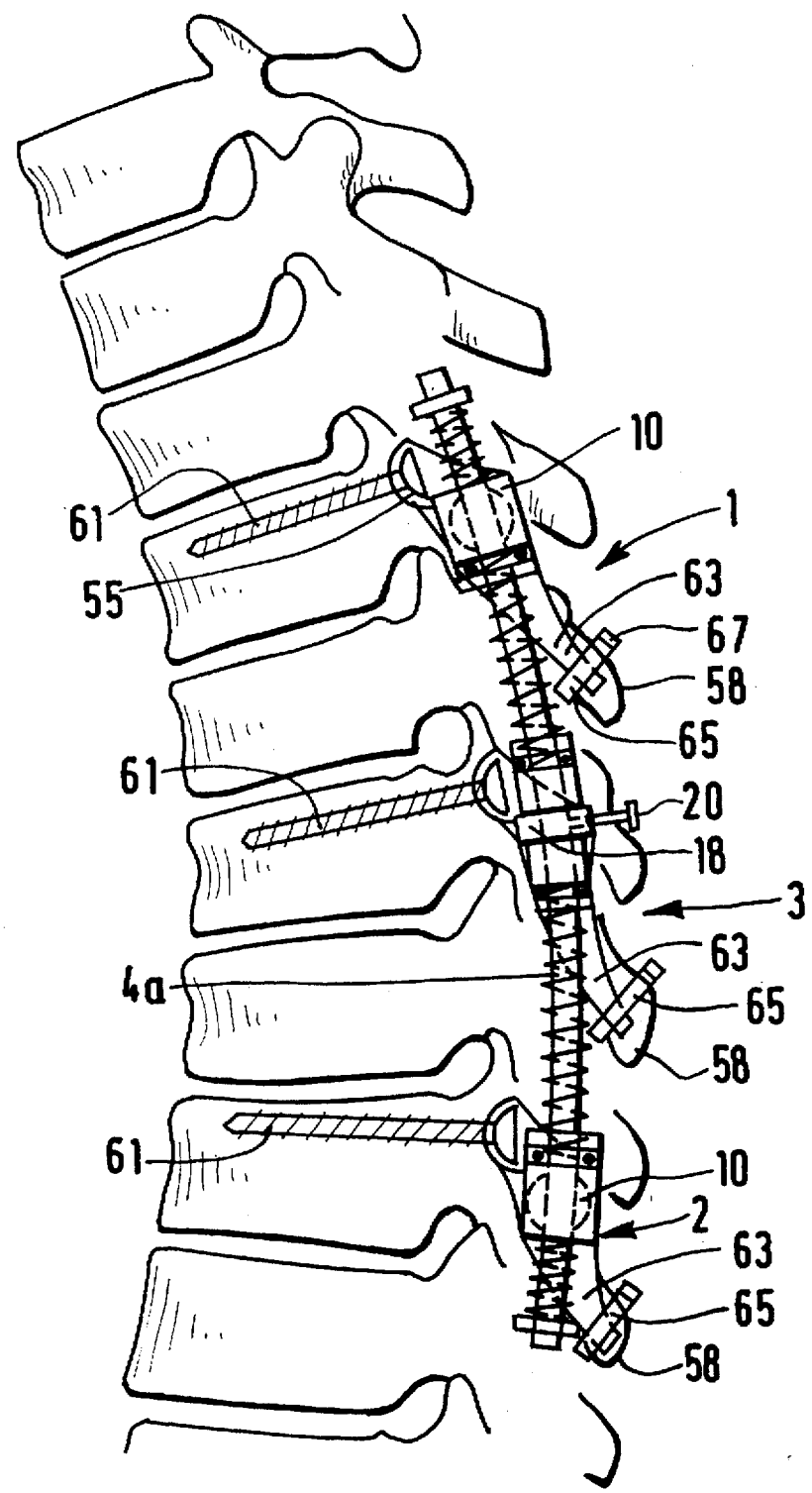
FIG. 2 is a diagrammatic view, in profile, of an implanted dynamic vertebral orthosis, which is more particularly intended for treating a scoliosis and is equipped with anchoring devices according to the invention.

FIG. 2 represents a view, in profile, of a variant form of embodiment of the orthosis previously described. As can be seen, the deflection of the rod 4a makes it possible to reestablish and maintain physiological cyphosis.

FIGS. 3 to 9 represent various modes of embodiment of the anchoring devices 1, 2, 3. According to the invention, the anchoring devices 1, 2, 3 for each vertebra have at least one plate 55 having an anterior convex face 56 which bears, with contact, against the vertebral posterior arch and, in particular, at least against the vertebral lamina 57 and/or on at least one side of the spinous process 58. The shape of the said convex face 56 therefore corresponds to that of the posterior face of the vertebral lamina 57. The convex face 56 may be constituted by porous metal of the "diamond point" type and is advantageously covered with hydroxy apatite in order to permit better cohesion with the bone. The coupling means are carried by a plate 55 on the anchoring devices. More precisely, the cylinders 10, 18, which are integral with the anchoring devices, are supported by a plate 55 facing the transverse end of the lamina 57, that is to say in the vicinity of the transverse process 59.

According to the invention, the anchoring devices 1, 2, 3 have anchoring means in at least two distinct portions of each vertebra. Thus, each plate 55 on the anchoring devices extends facing the pedicle 60 of the vertebra, and can be fixed to the said vertebra on at least one pedicle 60 by an intrapedicular screw 61 with a milled head fitted into a corresponding perforation 62 in the plate 55.

Each plate 55 on the anchoring devices also advantageously extends facing the lateral faces of the spinous process 58, on each side, and likewise has means for anchoring onto the said spinous process 58. In order to accomplish this, the end 63 of the plate 55 lying opposite the spinous process 58 has a bulge 64 projecting in the frontal plane and in the horizontal direction so as to form a shoulder for retaining an encircling arrangement (which may be constituted by a self-locking collar made of metal or synthetic material) or a flange 65 surrounding the spinous process 58 and clamping the end 63 of the plate 55. The flange 65 may be constituted by a frame 66 surrounding the spinous process and the end 63 of the plate 55, and by a screw 67 which has a vertical axis and is fitted through a vertical threaded hole in the frame 66 and the free end of which is provided with a shoe 68 which is supported on the upper face of the spinous process 58.

Thus the frame 66 is locked with respect to the spinous process. The flange 65 likewise has a screw 69 with a frontal horizontal axis, which is fitted into a horizontal threaded hole in the frame 66 and the free end of which is provided with a shoe 70 which is supported on the end 63 of the plate 55 in order to clamp it laterally against the spinous process 58. After the screw 69 has been tightened, the retaining shoulder formed by the bulge 64 locks the flange 65 in horizontal translation with respect to the free end 63 of the plate 55, the shoe 70 coming up against the said bulge 64. The flange 65 links together the two plates 55a, 55b and thus constitutes common means for anchoring the said two plates 55a, 55b to the spinous process 58 of the vertebra.

Likewise, each plate 55 of the anchoring devices advantageously extends facing at least one transverse process 59 of the vertebra, and has means for anchoring onto a transverse process 59. The said anchoring means may be formed by at least one hook 71 (left-hand plate 55a in FIG. 3) which is articulated, at the transverse end 72 of the plate 55a, about a horizontal spindle 74 and is supported on the upper face and/or on the lower face of the transverse process 59. The transverse end 72 of the plate 55a therefore has, for each hook 71, a yoke 73 in which the hook 71 is articulated about its spindle 74. Each hook 71 is provided, at its opposite end from the transverse process, with a vertical screw 75 which is fitted into a threaded hole in the hook 71 and is supported on a horizontal surface of the bottom of the yoke 73 of the plate 55a in order to clamp the said hook 71 against the corresponding surface of the transverse process 59.

In FIG. 3, the means for anchoring the right-hand plate 55b have a clamping claw 35 formed by two hooks 36, 37 which are articulated, with respect to the plate 55b, about two horizontal parallel spindles 48, 49. In a variant which is not represented, anchoring onto the transverse process may be brought about by a self-locking clamping collar (similar to the one used on the spinous process) made of metal or synthetic material. Each hook 36, 37 is similar to the hook 71 described above and is mounted in a yoke 50, 51 in the plate 55b with a vertical clamping screw 53, 54 which is supported on a horizontal surface of the bottom of the yoke 50, 51 in order to clamp the said hook 46, 47 against the corresponding surface, the upper surface and the lower surface, respectively, of the transverse process 59. The respective free ends 46, 47 of the two hooks 36, 37 extend facing one another in an opposed manner and are clamped towards one another under the effect of the screws 53, 54, in order to imprison the transverse process 59. Instead of the two screws 53, 54, it is possible to provide a tightener having two reversed screw threads, which links the two hooks to one another and is accessible from the top or bottom in order to clamp or unclamp the two hooks 36, 37. A claw of this kind may also be provided for the left-hand plate 55a.

As can be seen in FIGS. 3 and 4, the anchoring devices may have two plates 55a, 55b, one on each side of the spinous process (as represented in FIGS. 1 or 3), and this may be the case whether the orthosis has two rods (FIG. 1) or only one rod (FIG. 3) on only one side of the spinous process. As a variant, only one plate 55 may be provided.

Figure 5:
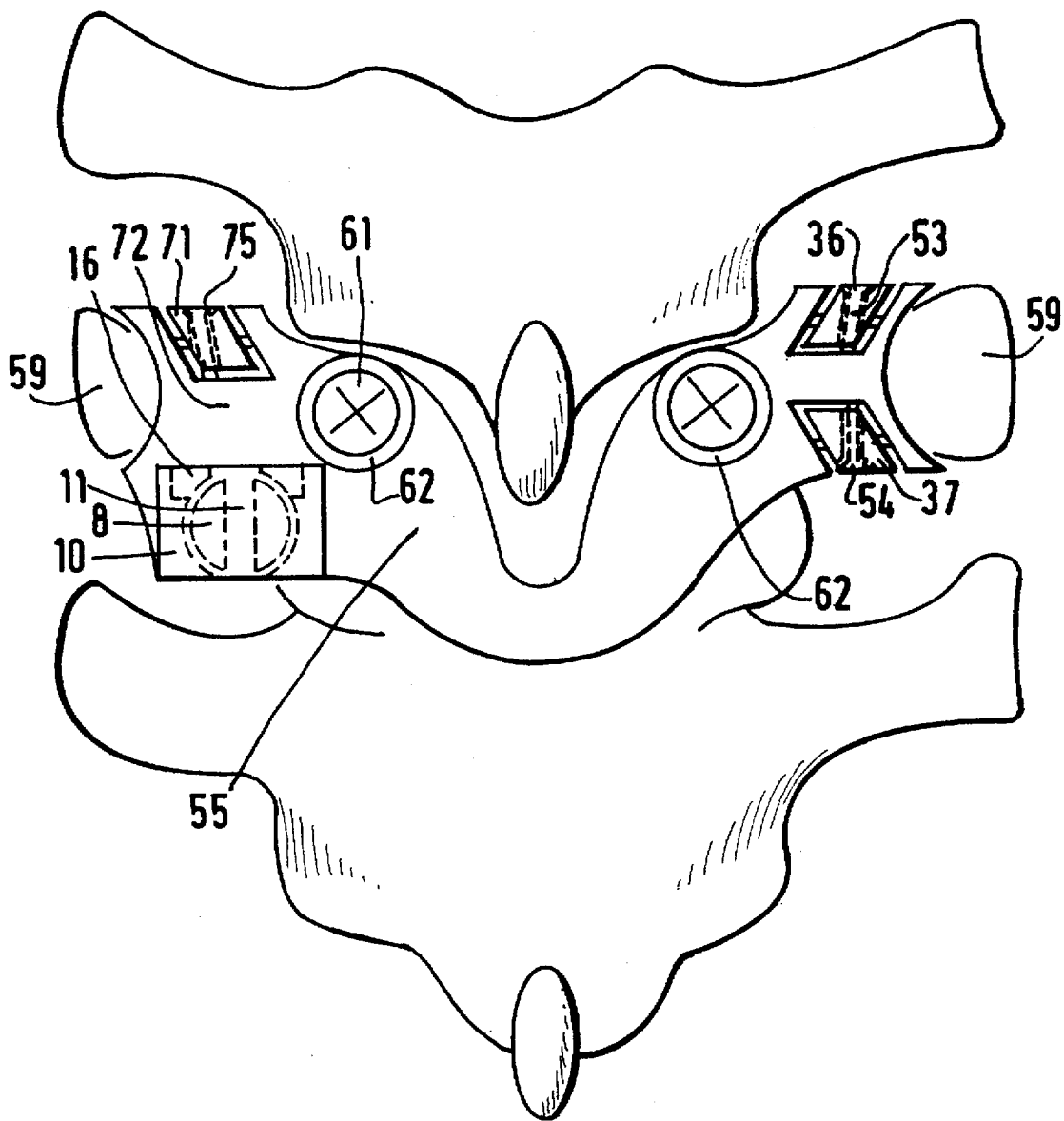
FIG. 5 is a diagrammatic rear view of a second mode of embodiment of an anchoring device according to the invention, which is intended for a vertebra devoid of a spinous process and/or of a lamina.

FIG. 5 represents a variant form of embodiment in which the plate 55 extends in the two paravertebral grooves, the vertebra not having any spinous process. The plate 55 is anchored onto the two transverse processes 59 and by the intrapedicular screws 61. The plate 55 forms a bridge covering the posterior vertebral arch and protecting the medullary canal.

Figure 6:
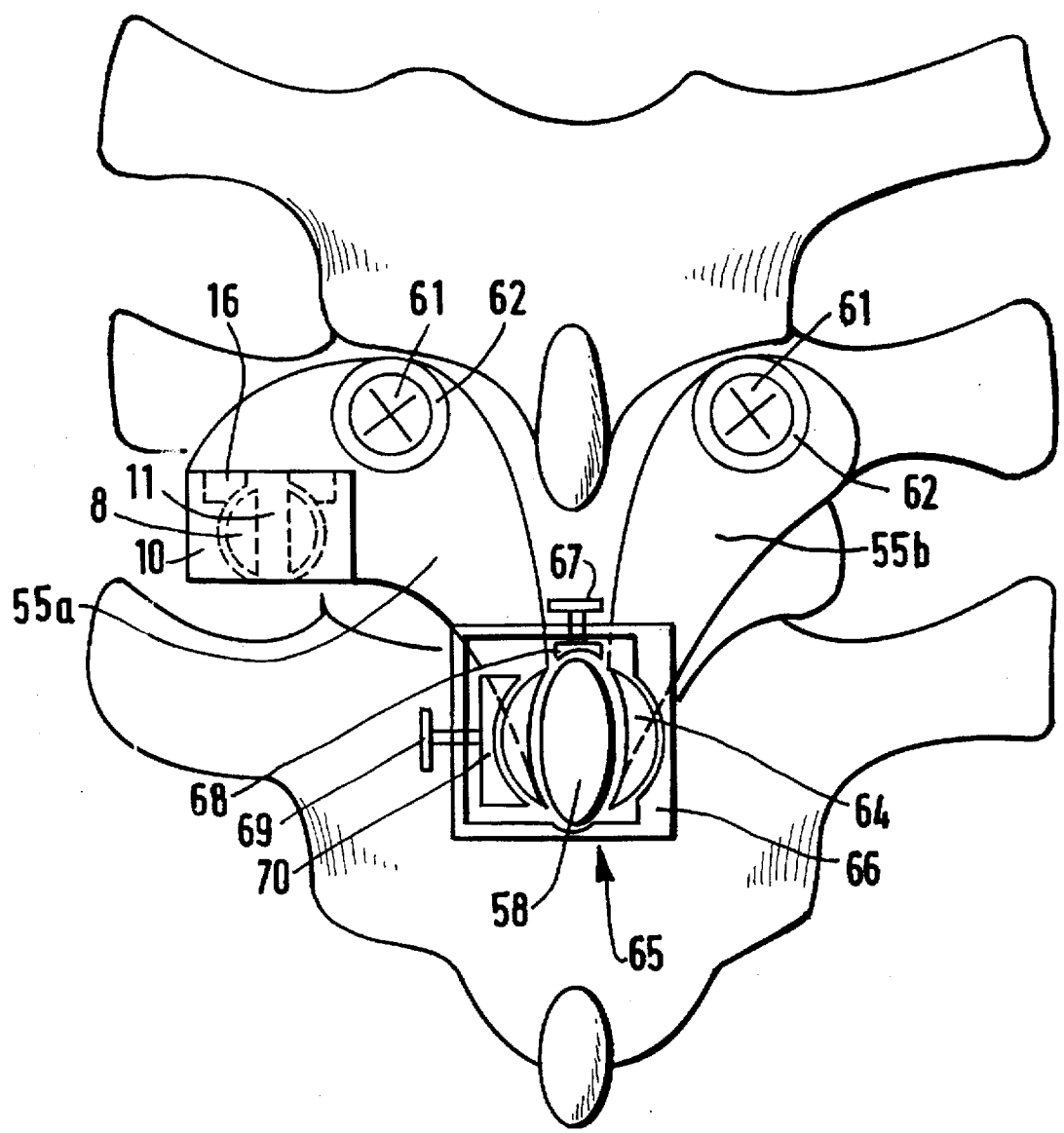
FIG. 6 is a diagrammatic rear view of a third mode of embodiment of an anchoring device according to the invention, without any support on the transverse processes.
Figure 7:
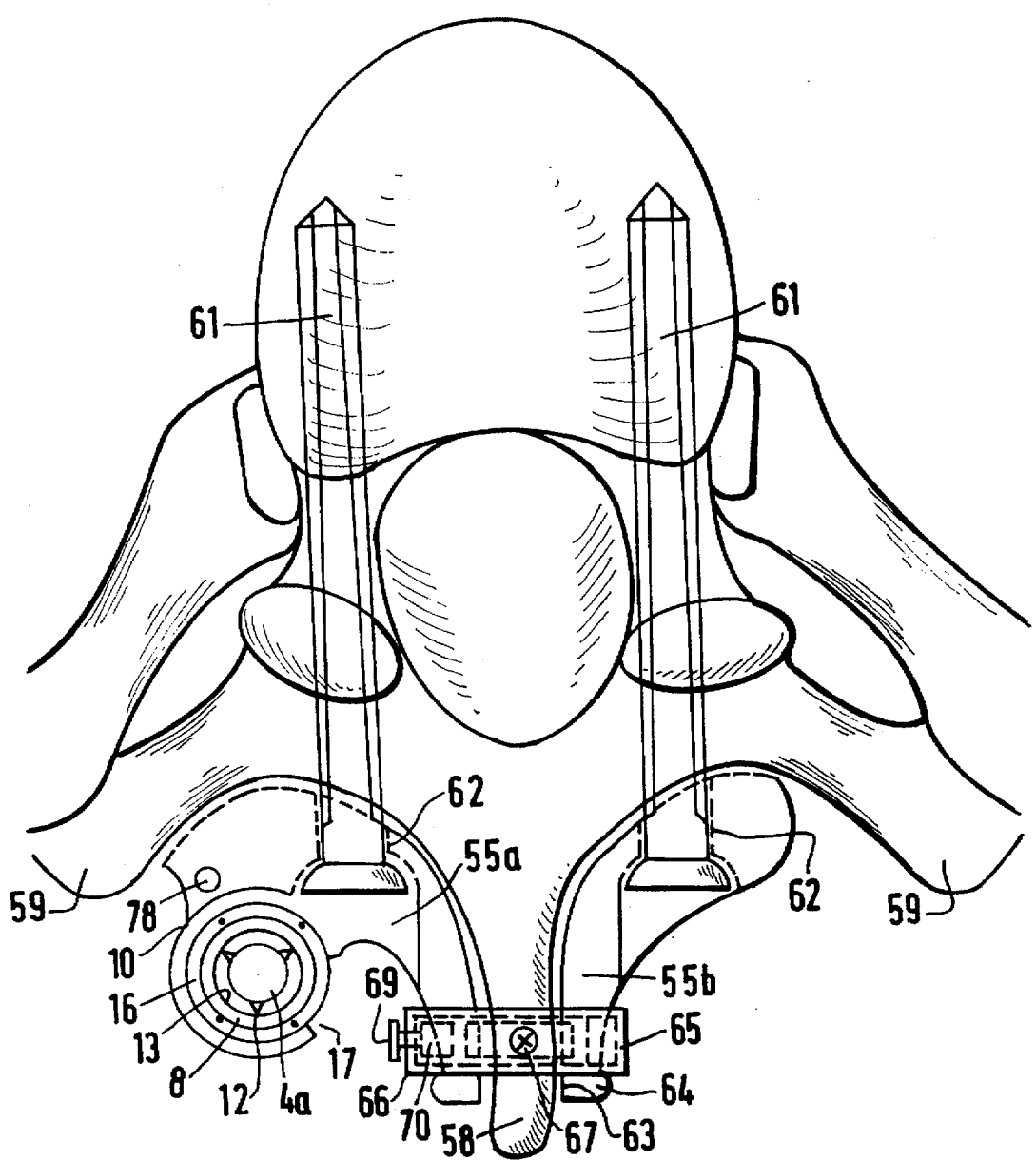
FIG. 7 is a diagrammatic view, in section through a horizontal plane, of FIG. 6.

FIGS. 6 and 7 represent another variant in which the plates 55 are anchored solely by the intrapedicular screws 61 and by the flange 65 onto the spinous process 58.

Figure 8:
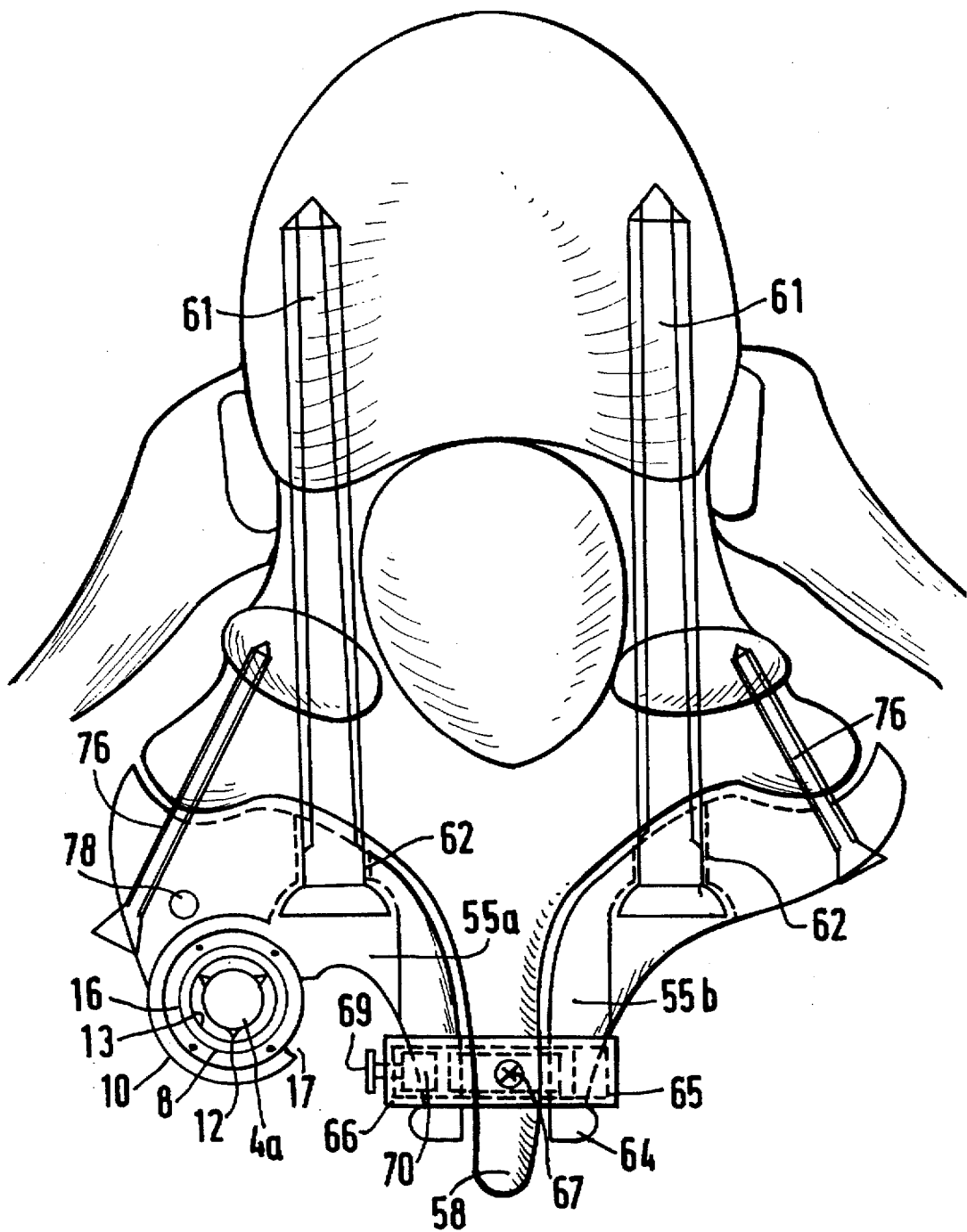
FIG. 8 is a diagrammatic view, in section through a horizontal plane, of a fourth mode of embodiment of an anchoring device according to the invention, which is intended for a vertebra such as the dorsal vertebra D12.
Figure 9:
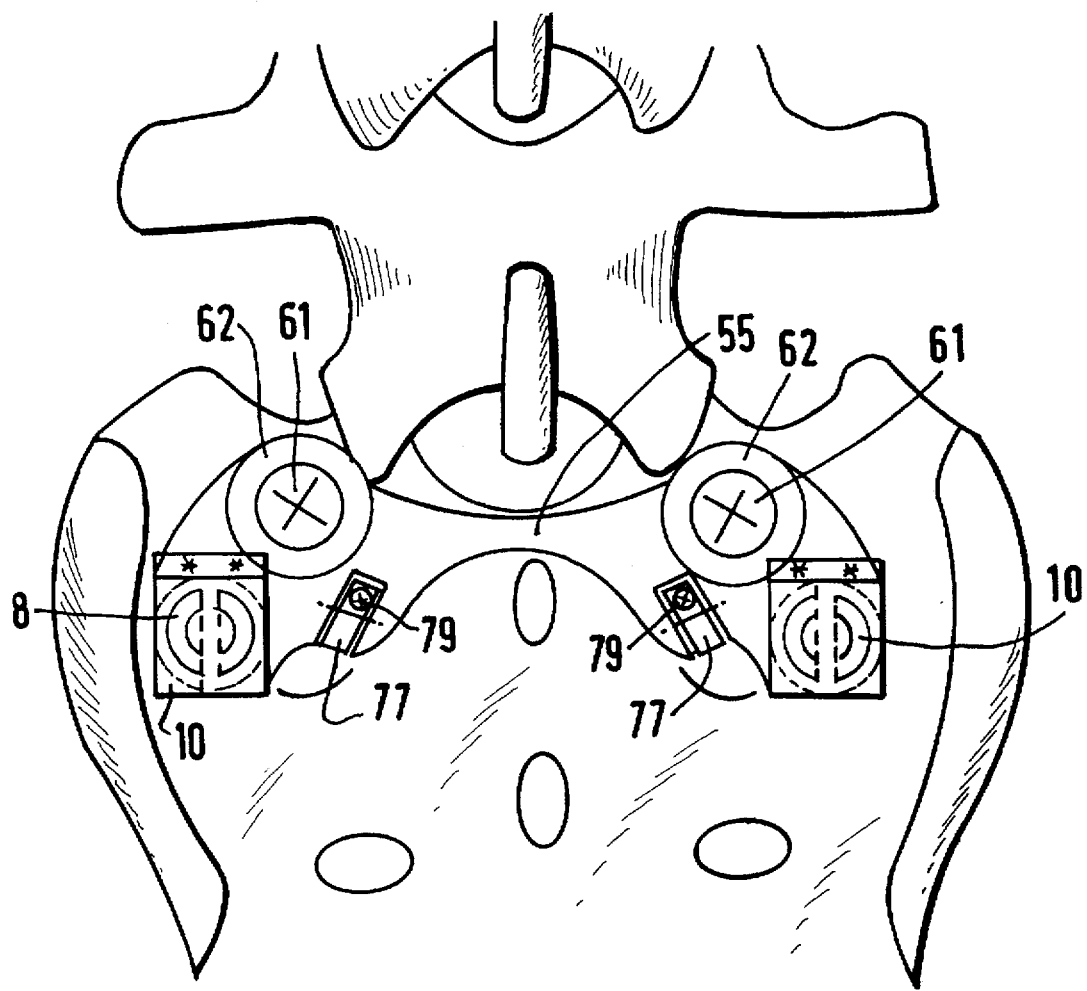
FIG. 9 is a diagrammatic rear view of a fifth mode of embodiment of an anchoring device according to the invention, which is intended for a sacral vertebra S1.

FIG. 8 represents another form of embodiment which is more specifically intended for the dorsal vertebra D12 which, generally speaking, does not have a transverse process. Each plate nevertheless fits the shape of the stump of the transverse process, to which stump it is fixed by an oblique screw 76 orientated in the direction of the pedicle. The plates 55 are also fixed by intrapedicular screws 61 and a clamping flange 65 onto the spinous process 58.

In the case of the sacral vertebra S1 (FIG. 9) which has no transverse process but a sacral ala, use is made of a continuous plate 55 extending on both sides of the spinous process while forming a bridge above the latter. The plate 55 may be anchored by two lower hooks 77 which are similar to the above-described hooks 71 of the transverse processes and are supported on the upper edges of the first two sacral holes. Each hook 77 is clamped by a clamping screw 79 which is fitted into a threaded hole in the hook and is supported on a vertical face of the plate 55. The plate 55 is fixed onto vertebra S1 by two intra-osseous screws 61 which pass through an orifice 62 provided in the plate and are directed, within the vertebral body of S1, towards its upper vertebral plateau. Two other screws (not represented) may stabilize the plate 55 by fixing it laterally to the sacral ala.

Figure 11:
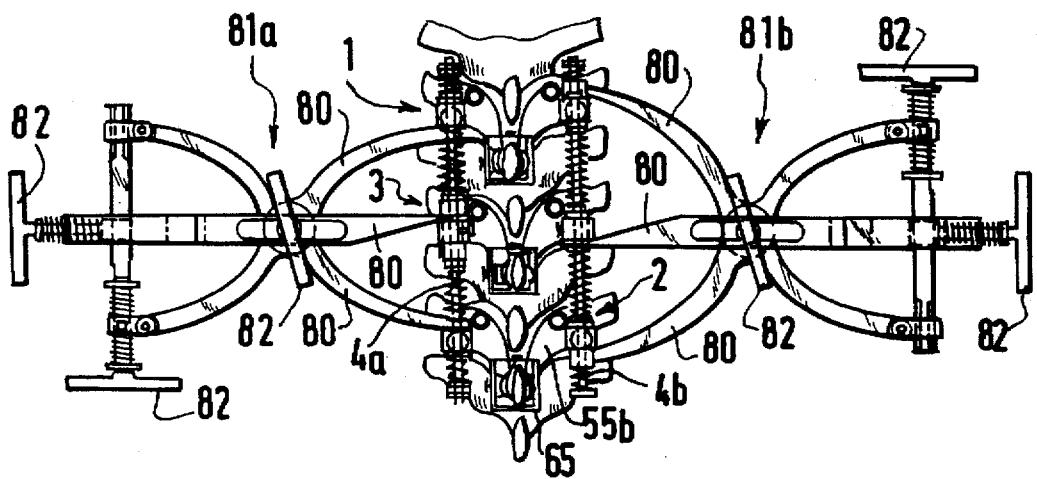
FIG. 11 is a diagrammatic rear view illustrating a later stage in the placing in position of an orthosis equipped with anchoring devices according to the invention.

As can be seen in FIG. 10 and 11, the anchoring devices 1, 2, 3 according to the invention make it possible, not only to bring about the anchoring of the orthosis onto the vertebrae, but also to effect a reduction in the corresponding scoliotic deformation and, immediately afterwards, the placing of the orthosis in position.

In order to accomplish this, each anchoring device 1, 2, 3 is provided, on each side of the spinous process 58, with a perforation 78 made through a horizontal extension of the plate 55 which carries means for coupling the rods 4a, 4b. Each perforation 78 is preferably made in the vicinity of the transverse process 59 and of the anterior and lateral side of a coupling cylinder 10, 18. The perforations, which have a vertical axis, permit the introduction of end studs on the sidepieces 80 of operative claws 81a, 81b. One claw 81a is located on the left-hand side, that is to say the same side as the concavity of the deformation to be reduced. On the other hand, another claw 81b is located on the right-hand side, that is to say on the same side as the convexity of the deformation to be reduced. The claws are supported on the anchoring devices 1, 2, 3. By operating the handles 82 of the operative claws 81a, 81b, a reduction in the deformation is obtained until the position represented in FIG. 11 is reached. The rods 4a, 4b and the springs, that is to say the instrumentation constituted by the orthosis, can then be linked to the various anchoring devices 1, 2, 3, when the claws 81a, 81b are maintaining the vertebral column in its corrected position. Once the instrumentation has been linked with the anchoring devices 1, 2, 3, the claws 81a, 81b can be withdrawn from the said anchoring devices 1, 2, 3.

Although the invention has been described with reference to a dynamic implanted vertebral orthosis for reducing a scoliosis, the anchoring devices according to the invention can be used for any other spinal instrumentation in which the same problems arise, namely a lumbar or sacro-lumbar orthosis for reducing intervertebral strains, a cervical orthosis, a spinal osteosynthesis device, for example of the Cotrel-Dubousset type, or other instrumentation.

I claim:

1. A device for anchoring spinal instrumentation onto a vertebra, comprising:
    at least one support plate having coupling means for coupling the instrumentation to said support plate, said support plate having a convex face shaped so as to conform to and bear against the concave surface of the vertebral posterior arch,
    anchoring means for anchoring said support plate with respect to the vertebra, and wherein
    a) the convex face of said at least one support plate extends facing at least one process or at least one sacral hole of the vertebra,
    b) said anchoring means comprising means for anchoring at least two distinct portions of said support plate onto at least two corresponding distinct parts of the vertebra selected from (i) the spincos process of the vertebra, (ii) a transverse process of the vertebra, (iii) a pedicle of the vertebra, and (iv) a sacral hole of the vertebra,
    c) said anchoring means further comprising means for anchoring said support plate onto at least one process or sacral hole of the vertebra,
    d) said anchoring means also comprising a claw, an encircling arrangement, or a flange surrounding said process for clamping onto said process.

2. A device as in claim 1 and wherein said anchoring means comprises means for anchoring said support plate onto the spinous process of the vertebra.

3. A device as in claim 1 and wherein said anchoring means comprises means for anchoring said support plate onto at least one transverse process of the vertebra.

4. A device as in claim 1 and wherein said anchoring means comprises means for anchoring said support plate with respect to at least one pedicle of the vertebra.

5. A device as in claim 1 and wherein said convex face has a shape corresponding to posterior face of the vertebral lamina.

6. A device as in claim 1 and wherein said support covers a portion of the concave surface of the posterior arch of the vertebra on at least one side of the spinous process.

7. A device as in claim 2 and wherein said device includes two supports, one on each side of the spinous process.

8. A device as in claim 7 and wherein one of said supports carries said coupling means.

9. A device as in claim 7 and wherein each of said supports carries coupling means for coupling the instrumentation to said support plate.

10. A device as in claim 7 and wherein said two supports are linked to the spinous process by one anchoring means.

11. A device as in claim 1 and wherein said anchoring means comprises a hook having a free end and articulated about a spindle on said support plate, said hook including a clamping screw threadedly engaging said hook, said screw being supported on said support plate in such a manner that said hook is pivotable about said spindle in the direction in which said free end is clamped onto the vertebra.

12. A device as in claim 11 and including two of said hooks having mutually facing free ends clamped toward each other.

13. A device as in claim 1 and wherein the convex face of said support plate is formed of porous metal.

14. A device as in claim 1 and wherein the convex face of said support plate is covered with a layer of hydroxy apatite.

* * * * *